(12) United States Patent
Zimmerman et al.

(10) Patent No.: US 6,391,334 B1
(45) Date of Patent: May 21, 2002

(54) BARRIER-FORMING COMPOSITION

(75) Inventors: Amy C. Zimmerman, Grand Rapids; John V. Scimeca, Kentwood, both of MI (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/426,428

(22) Filed: Oct. 25, 1999

(51) Int. Cl.$^7$ .................. A61K 31/722; A61K 7/40; A61K 9/70; A61K 31/164
(52) U.S. Cl. .................. 424/443; 424/402; 514/55; 514/613
(58) Field of Search .................. 514/55, 613; 424/401, 424/402, 443, 78.03

(56) References Cited

U.S. PATENT DOCUMENTS

| | | | |
|---|---|---|---|
| 4,599,209 A | 7/1986 | Dautzenberg et al. | 264/7 |
| 4,772,689 A | 9/1988 | Lang et al. | 536/20 |
| 4,772,690 A | 9/1988 | Lang et al. | 536/20 |
| 4,780,310 A | 10/1988 | Lang et al. | 424/47 |
| 4,845,204 A | 7/1989 | Lang et al. | 536/20 |
| 4,923,977 A | 5/1990 | Lang et al. | 536/20 |
| 5,057,542 A | 10/1991 | Leuba et al. | 514/844 |
| 5,405,314 A | 4/1995 | Ohta et al. | 602/49 |
| 5,420,197 A | 5/1995 | Lorenz et al. | 525/54.3 |
| 5,496,872 A | 3/1996 | Constancis et al. | 523/118 |
| 5,686,089 A | * 11/1997 | Mitra et al. | 424/405 |
| 5,750,122 A | * 5/1998 | Evans et al. | 424/401 |
| 5,902,798 A | 5/1999 | Gouda et al. | 514/55 |

FOREIGN PATENT DOCUMENTS

JP  57-180602 A  11/1982

* cited by examiner

*Primary Examiner*—Edward J. Webman
*Assistant Examiner*—Helen Nguyen
(74) *Attorney, Agent, or Firm*—Brinks Hofer Gilson & Lione

(57) ABSTRACT

A composition comprising panthenol or a derivative thereof, chitosan or a derivative thereof, and a carrier, wherein the composition forms a barrier that enhances the removal of an object having an adhesive-containing surface from a another surface to which the composition is applied without substantially interfering with the ability of the adhesive to adhere to the other surface.

12 Claims, No Drawings

BARRIER-FORMING COMPOSITION

The present invention relates to a barrier-forming composition. In particular, the present invention is directed to a composition that, when applied to a surface, enhances the removal of an object having an adhesive-containing surface from the surface to which the composition is applied without substantially interfering with the ability of the adhesive to adhere to the surface. Preferentially, the composition is used to pre-treat skin (or hair or nails, all of which are examples of "a surface") before adhering to the skin an object having an adhesive-containing surface. The barrier-forming composition significantly reduces redness and/or irritation that may be caused by the removal of the adhesive-containing surface from the skin.

Presently, when an object having an adhesive-containing surface is placed on another surface so that the object adheres to the other surface, removal of the objects may cause harm to the other surface. Such "other surfaces" include but are not limited to skin (mammalian or otherwise), hair and nails. For example, when an object having an adhesive-containing surface is placed on skin, removal of the object causes irritation and redness of the skin. Such "objects" include but are not limited to bandages, anti-smoking patches, and magnet-therapy discs.

This irritation can be addressed by pre-treating the other surface with a composition such as an aloe gel. A problem with pre-treating the other surface with aloe gel is that aloe gel can interfere with the ability of the adhesive surface to adhere to the other surface. For example, applying aloe gel to skin before applying a bandage would render the adhesive surface of the bandage useless. The bandage would simply slide off of the skin.

Surprisingly and unexpectedly, it has been found that a composition comprising panthenol, chitosan, and a suitable carrier forms a barrier on certain surfaces that enhances the removal of an object having an adhesive-containing surface from another surface without substantially interfering with the ability of the adhesive surface to adhere to the other surface. Panthenol, by itself, creates a thick, sticky film. Chitosan, by itself, creates a very thin film. Together in the same composition, panthenol and chitosan complement each other to form a pleasant barrier-forming composition.

SUMMARY OF THE INVENTION

The present invention provides a composition comprising panthenol or a derivative thereof, chitosan or a derivative thereof, and a carrier, wherein the composition forms a barrier that enhances the removal of an object having an adhesive-containing surface from another surface to which the composition is applied without substantially interfering with the ability of the adhesive to adhere to the other surface.

In another aspect, the present invention provides a method of forming a barrier on a surface that enhances the ease from which an object having an adhesive-containing surface is removable from the surface without substantially interfering with the ability of the adhesive to adhere to the surface. The method comprises applying a composition to the surface, where the composition comprising panthenol or a derivative thereof, chitosan or a derivative thereof, and a carrier.

In another aspect, the present invention provides a composition comprising by weight from about 0.1% to about 10% panthenol or a derivative thereof, from about 0.1 % to about 15% chitosan or a derivative thereof, from about 5% to about 95% water, from about 0.1% to about 5% glycerin or a glycerin derivative, and from about 5% to about 95% alcohol.

All percentages referred to in the specification and claims are by weight unless otherwise stated.

DETAILED DESCRIPTION OF THE PREFERRED EMBODIMENTS

Generally, the invention provides a composition comprising panthenol or a derivative thereof, chitosan or a derivative thereof, and a carrier, wherein the composition forms a barrier that enhances the removal of an object having an adhesive-containing surface from another surface to which the composition is applied without substantially interfering with the ability of the adhesive to adhere to the other surface.

Panthenol or its derivatives are contemplated for use with this invention. Panthenol is an effective film-forming compound having the following structure:

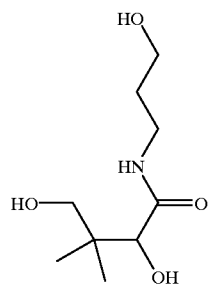

Panthenol equivalents may include alcohol derivatives of pantothenic acid, such as the ones described in CTFA Cosmetic Ingredient Handbook, The Cosmetic, Toiletry and Fragrance Association. Inc., pp. 272–273, 1992. Suitable derivatives may include panthenol's enantiomers or d-panthenol, preferably d-panthenol. The preferable form of panthenol is soluble in both alcohols and polar solvents and it is commercial available.

The panthenol or its derivative may be present in the composition in an amount of from about 0.1 % to about 10%, more preferably from about 1% to about 5%, and most preferably from about 1.5% to about 2.5%. For optimal usefulness, the amount of panthenol should be chosen so that the composition dries reasonably quickly. The more panthenol in the composition, the longer it takes for the composition to dry when it is applied to skin or other surfaces.

Chitosan or its derivatives are contemplated for use with this invention. Chitosan and its derivatives are effective film-forming compounds. Chitosan and its derivatives generally form a much thinner film than panthenol.

Chitosan is also known as beta-(1,4)-2-amino-2-deoxy-D-glucose; beta-1,4-Poly-D-glucosamine; deacetylated chitin; poly-D-glucosamine; and poliglusam. Chitosan is a partially deacetylated polymer of acetol glucosamine (2 acetamido-2 deoxy b-1,4-D-glucan). It is a natural, water-soluble derivative of cellulose.

Chitosan can be used as a flocculent, clarifier, thickener, fiber, film, affinity chromatography column matrix, gas-selective membrane, plant disease resistance promoter, anti-cancer agent, wound healing promoting agent and antimicrobial agent. It can be used in pet food and is generally regarded as safe. It is used as a processing aid, and may possibly be used in fruit preservation, wound dressings, cosmetics, artificial organs and pharmaceuticals.

Chitosan is usually prepared from chitin, and chitin has been found in a wide range of natural sources, including crustaceans, fungi, insects, annelids, mollusks, and coelenterata. Chitosan, however, is primarily manufactured from crustaceans such as crab krill and crayfish because a large amount of the crustacean exoskeleton is available as a by-product of food processing.

Preferably, the chitosan derivative used in the present invention is hydroxy propyl chitosan.

The chitosan or a chitosan-derivative may present in the composition of the present invention in an amount of from about 0.1% to about 15%, more preferably from about 2% to about 10%, and most preferably from about 3% to about 5%.

The present invention contemplates the use of any cosmetically-acceptable carrier that does not interfere with the ability of the composition to form a barrier that enhances the ease from which an object having an adhesive surface is removable from another surface without interfering with the ability of the adhesive surface to adhere to the other surface. Preferred carriers include water, alcohol, glycerin and glycerin derivatives, volatile silicones, low molecular weight esters, and mixtures thereof.

A non-limiting list of alcohols that may be used with this invention include methanol, ethanol, 1-propanol, 2-propanol, 1-butanol, 1,1-dimethyl ethanol, 2-methyl-1-propanol, 1-pentanol, 2-pentanol, 3-pentanol, 2-methyl-1-butanol, 3-methyl-1-butanol, 2-hexanol, 3-methyl-1-pentanol, 3-methyl-1-pentanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and 1-dodecanol, and the like. Preferably, the alcohols have from 1 to 18 carbon atoms, and more preferably 1 to 12 carbon atoms, with the average number of carbon atoms being about 4 to 18.

The carrier may also contain low molecular weight esters, so long as such esters are sufficiently volatile as to not interfere with the ability of the adhesive to adhere to a surface to which the carrier is applied. Such esters may include but are not limited to methyl acetate, ethyl acetate, propyl acetate, isopropyl acetate, butyl acetate, methyl propionate, ethyl propionate, propyl propionate, isopropyl propionate, butyl propionate, methyl butanoate, ethyl butanoate, propyl butanoate, methyl benzoate, ethyl benzoate and the like.

The carrier may also contain silicone-containing compositions, so long as the silicone in the composition was sufficiently volatile as to not interfere with the ability of the adhesive to adhere to the other surface. The volatile silicones may be cyclic silicones having the general formula:

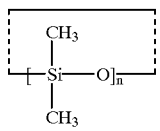

wherein n=3–7.

The linear volatile polydimethylsiloxanes have from about 3 to 9 silicon atoms and have the general formula:

where n=1–7

As n increases over 7, the silicone becomes increasingly nonvolatile.

Silicones of the above types, both cyclic and linear, are available from Dow Corning Corporation, Dow Corning 344, 345, and 200 fluids; Union Carbide, Silicone 7202 and Silicone 7158; and Stauffer Chemical SWS-03314. The linear volatile silicones generally have viscosities of less than about 5 centipoise at 25° C., while the cyclic materials have viscosities less than about 10 centipoise. The term "volatile" means that the material has a measurable vapor pressure. Preferably, any silicone-containing composition in the carrier would comprise less than about 10% by weight of the entire barrier-forming composition.

Other cosmetically-acceptable carriers that do not interfere with the barrier-forming ability of the panthenol and chitosan are within the scope of this invention.

Uses And Delivery Vehicles

One use of the composition of the present invention is to pre-treat skin, hair, or nails before applying an object having an adhesive-containing surface to the skin, hair, or nails. To this end, skin (mammalian or otherwise) is contemplated one of the many possible "other surfaces." In this use, "objects having adhesive-containing surfaces" include bandages, anti-smoking patches, and magnet therapy discs, as well as many other objects.

In this use of the composition, the composition forms a barrier that allows the adhesive-containing surface to adhere to the skin, yet it enhances the ease from which the object having the adhesive-containing surface is removable from skin. That is, the barrier allows the object to be removed from the skin without the same level of skin redness and irritation normally associated with removing an object having an adhesive-containing surface from skin.

For a very specific but non-limiting example, applying the composition of the present invention before applying a bandage will make the bandage all the easier to remove when the time for removal is appropriate. Further, the barrier will not prevent the bandage from adhering to the skin.

There are several possible ways to deliver the composition of the present invention to skin. For example, the composition may be delivered via a pre-moistened piece of material such as a towellete, paper, or non-woven material. It can also be delivered via a brush, a bottle, a tube, a roller, a pad, and any other delivery mechanism from which the composition can easily and conveniently be applied to a surface.

EXAMPLES

The following are illustrative examples of formulations and compositions according to this invention and it should be understood that they do not limit the scope of the invention.

Example 1

| Ingredient | amount (wt %) |
| --- | --- |
| Panthenol | 2 |
| Hydroxy propyl chitosan | 4 |
| Glycerin | 1 |
| Butylene glycol | 2 |
| SD alcohol | 80 |
| Water | 11 |
| TOTAL | 100 |

Example 2

| Ingredient | amount (wt %) |
|---|---|
| Panthenol | 2 |
| Hydroxy propyl chitosan | 4 |
| Glycerin | 1 |
| Butylene glycol | 2 |
| SD alcohol | 20 |
| Water | 71 |
| TOTAL | 100 |

It should be understood that a wide range of changes and modifications can be made to the embodiments described above. It is therefore intended that the foregoing description illustrates rather than limits this invention, and that it is the following claims, including all equivalents, which define this invention.

What is claimed:

1. A composition comprising:
   a. panthenol or a derivative thereof;
   b. chitosan or a derivative thereof; and
   c. a carrier, wherein the composition forms a barrier that enhances the removal of an object having an adhesive-containing surface from an epidermal surface to which the composition is applied without substantially interfering with the ability of the adhesive to adhere to the epidermal surface.

2. The composition of claim 1 wherein the composition comprises from about 0.1% to about 10% by weight of panthenol or a derivative thereof.

3. The composition of claim 1 wherein the composition comprises from about 1% to about 5% by weight of panthenol or a derivative thereof.

4. The composition of claim 1 wherein the composition comprises from about 1.5% to about 2.5% by weight of panthenol or a derivative thereof.

5. The composition of claim 1 wherein the chitosan derivative is hydroxy propyl chitosan.

6. The composition of claim 1 wherein the composition comprises from about 0.1% to about 15% by weight of chitosan.

7. The composition of claim 1 wherein the composition comprises from about 2% to about 10% by weight of chitosan.

8. The composition of claim 1 wherein the composition comprises from about 3% to about 5% by weight of chitosan.

9. The composition of claim 1 wherein the epidermal surface is human skin.

10. A towelette containing the composition of claim 1.

11. A composition comprising by weight:
   a. from about 0.1% to about 10% panthenol or a derivative thereof,
   b. from about 0.1% to about 15% chitosan or a derivative thereof;
   c. from about 5% to about 95% water;
   d. from about 0.1% to about 5% glycerin; and
   e. from about 5% to about 95% alcohol.

12. A towellete containing the composition of claim 11.

* * * * *